United States Patent [19]

Groves

[11] 4,065,357

[45] Dec. 27, 1977

[54] DETECTION OF CATALASE-CONTAINING BACTERIA

[75] Inventor: James N. Groves, Schenectady, N.Y.

[73] Assignee: General Electric Company, Schenectady, N.Y.

[21] Appl. No.: 632,483

[22] Filed: Nov. 17, 1975

Related U.S. Application Data

[60] Continuation of Ser. No. 434,999, Jan. 21, 1974, abandoned, which is a division of Ser. No. 886,283, Dec. 18, 1969, Pat. No. 3,838,034, which is a continuation-in-part of Ser. No. 723,179, April 22, 1968, abandoned.

[51] Int. Cl.$^2$ ............................................. G01N 31/14
[52] U.S. Cl. .............................................. 195/103.5 R
[58] Field of Search ............. 195/103.5 R; 204/195 P

[56] References Cited

U.S. PATENT DOCUMENTS 3,564,588  2/1971  Soli .............................. 195/103.5 R
3,933,593  1/1976  Sternberg ...................... 195/103.5 R

OTHER PUBLICATIONS

Roxth et al., Biochim. et Biophys. Acta, 139, (1967), pp. 171-173.

Primary Examiner—Alvin E. Tanenholtz
Assistant Examiner—Esther M. Kepplinger
Attorney, Agent, or Firm—Jane M. Binkowski; Joseph T. Cohen; Jerome C. Squillaro

[57] ABSTRACT

Sensitive, fast-response apparatus is described for the detection of the presence of (a) aerobic or facultatively anaerobic bacteria, (b) certain body cell breakdown products in body fluids or (c) unusual contamination of the ambient by aerobic bacteria. The method employed, which enables dynamic, continuous observation of catalase-$H_2O_2$ reaction, is based upon measuring the incremental increase of oxygen partial pressure within a hydrogen peroxide solution. The inherent catalase content in such bacteria and in most animal cells promotes the rapid decomposition of hydrogen peroxide resulting in the liberation of oxygen. This measurement of oxygen partial pressure is made directly from the hydrogen peroxide solution by means of an oxygen permeable membrane polarographic cell equipped with a cathode configuration providing improved sensitivity. The presence of small numbers of bacteria or other catalase-containing cells may be quantitatively determined by conducting the catalase-$H_2O_2$ reaction in a very small reproducible reaction volume.

4 Claims, 12 Drawing Figures

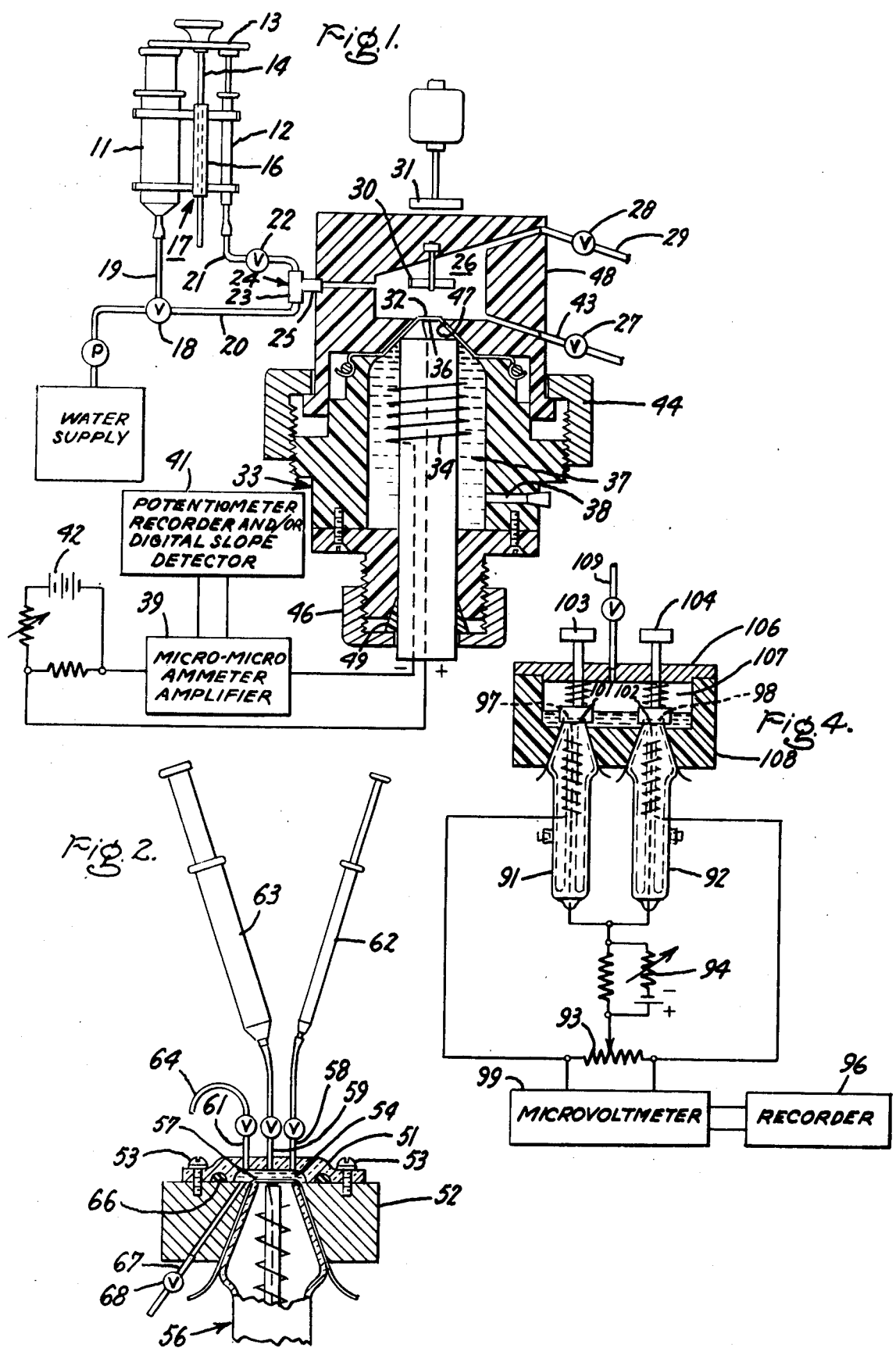

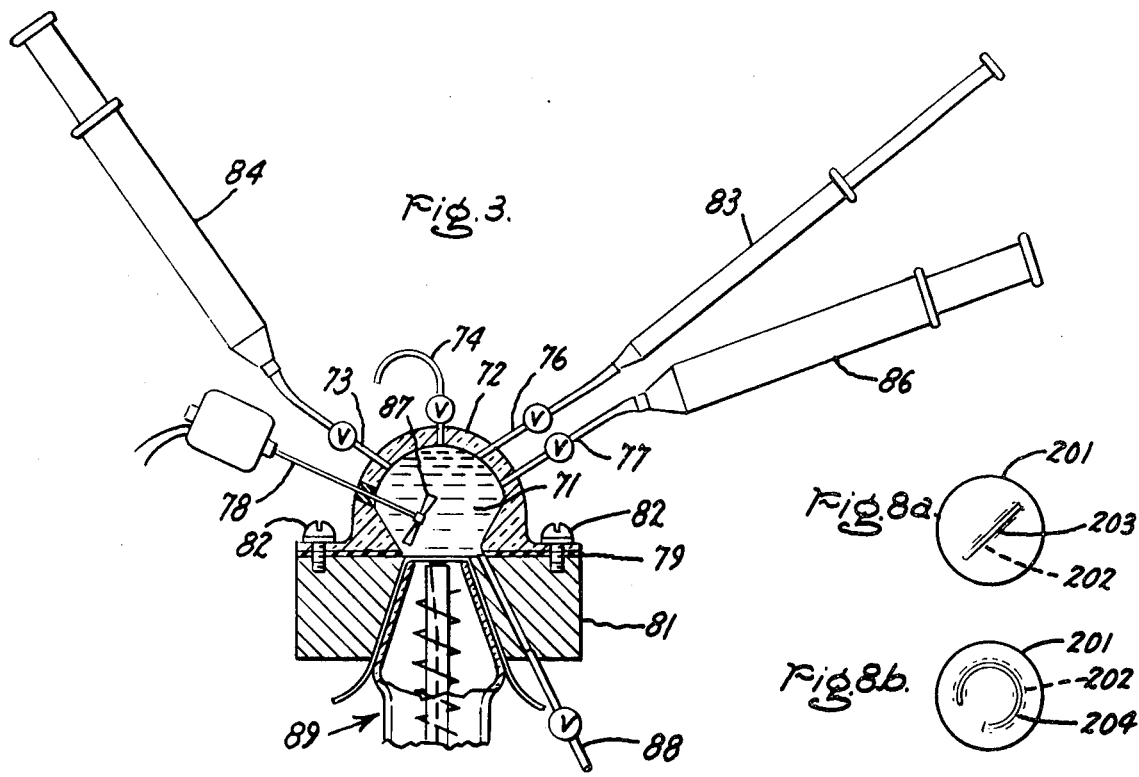
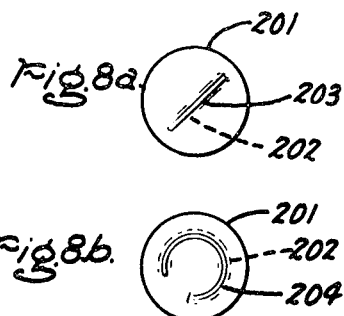
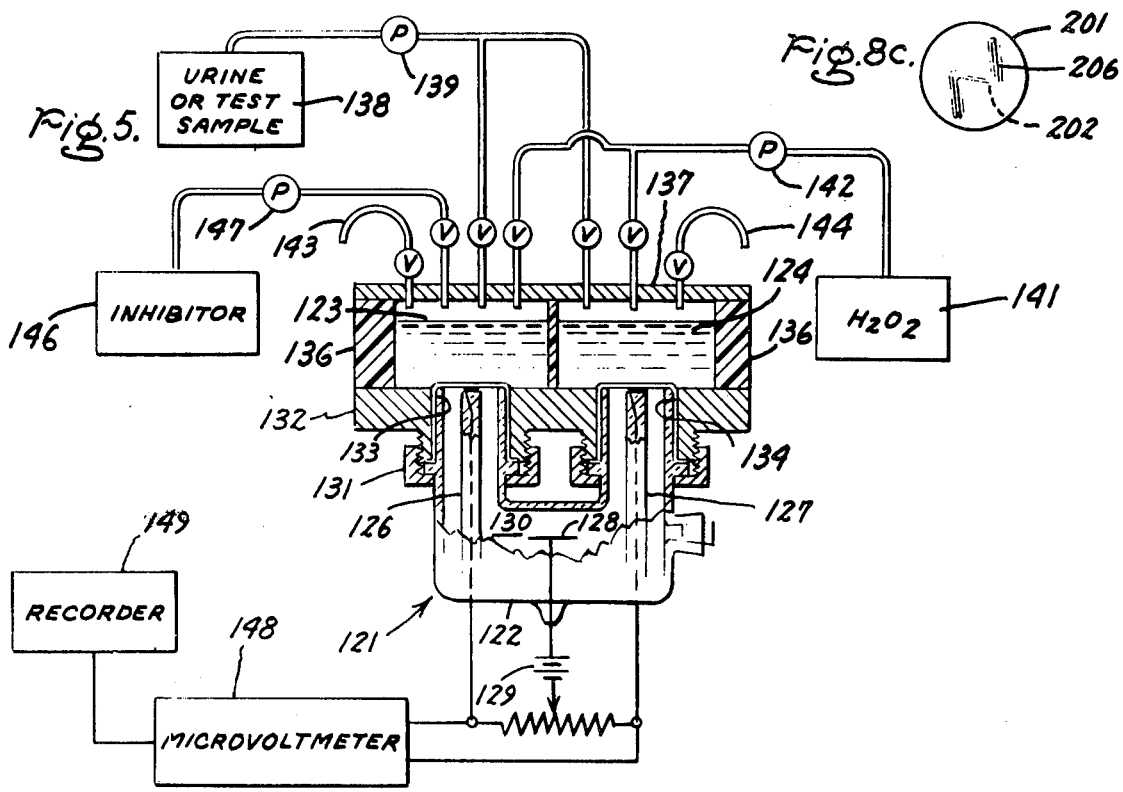

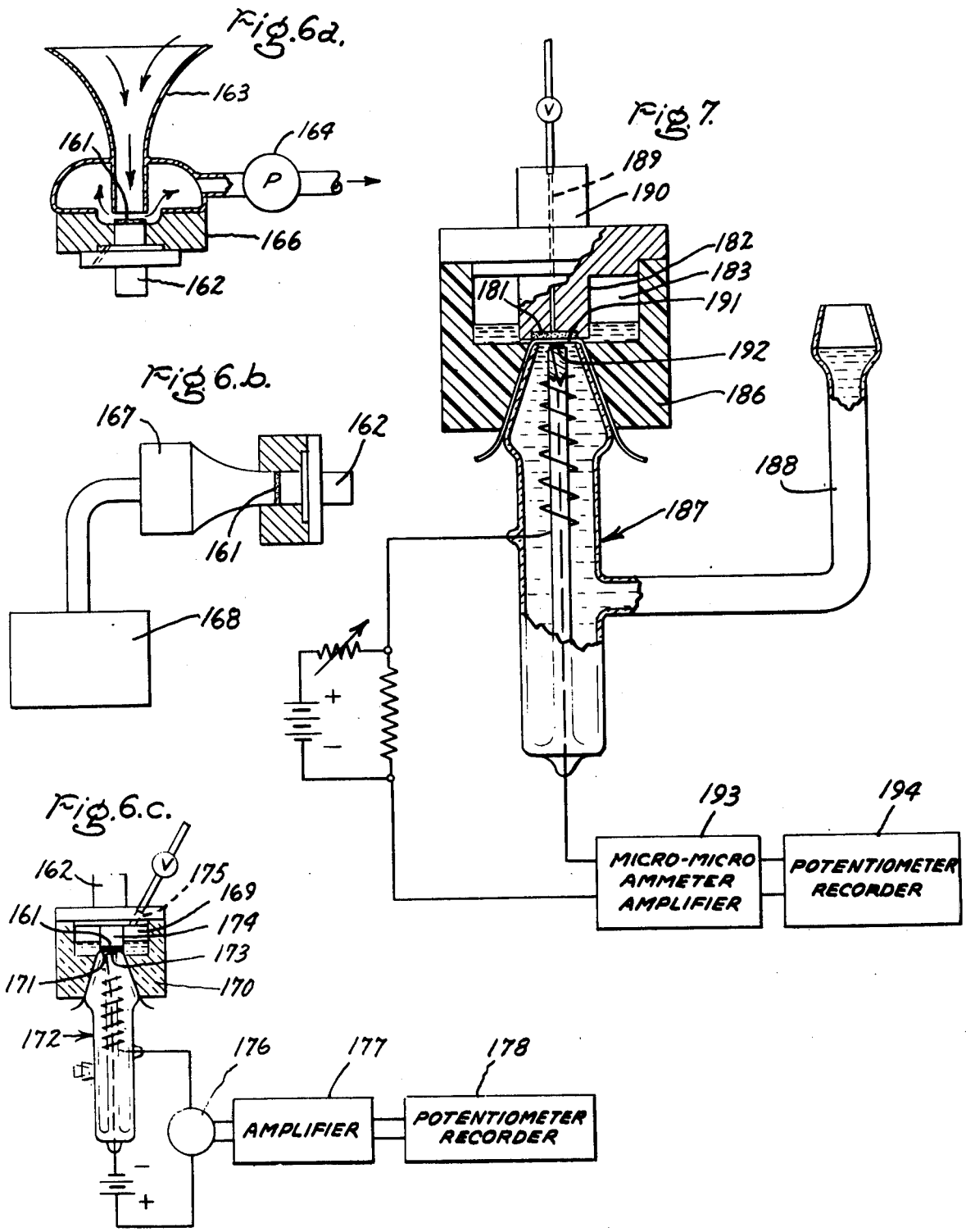

ately detect an increase within a hydrogen
DETECTION OF CATALASE-CONTAINING BACTERIA This is a continuation of application Ser. No. 434,999, filed Jan. 21, 1974, now abandoned which is a Division of application Ser. No. 886,283 filed Dec. 18, 1969 now U.S. Pat. No. 3,838,034 which is a Continuation-in-part of abandoned application Ser. No. 723,179, filed Apr. 22, 1968.

BACKGROUND OF THE INVENTION

Conventional bacteriological culturing techniques for the detection of bacteria are time consuming (requiring a minimum time of 24 hours), expensive (because of the labor involved) and are not as accurate as would be desirable.

In the past studies have been made of the activity of the enzyme catalase. In such studies bacteria and hydrogen peroxide have been brought together thereby generating a reaction between the catalase present in the bacteria causing the release of oxygen. The released $O_2$ entering the free volume above the $H_2O_2$ solution causes an increase in gas pressure. Attempts to measure this change in gas pressure (as with a manometer) have been made, but this method is definitely limited in speed of response. This limitation prevents dynamic monitoring of the catalase-$H_2O_2$ reaction, which proceeds very rapidly. Also, the inherent lack of sensitivity of this type of measurement dictates against the use thereof for the quantitative measure of catalase activity.

Catalase activity has also been quantitatively measured by titration for the remaining $H_2O_2$ after some preselected reaction period, but this method is cumbersome and inconvenient, would be very difficult to use for dynamic monitoring and offers no opportunity for continuous recording of the reaction.

There is a continuing and pressing need for a sensitive fast-response quantitative bacteria detector for use in identifying pathological conditions, in testing for water pollution, in processing foods, in defending against biological warfare, and in environmental control. Further, there is need for means to dynamically and continuously observe and record the catalase-$H_2O_2$ reaction. These needs have been satisfied by various adaptions of the intant invention to be described herein.

THEORY AND SUMMARY OF THE INVENTION

Most pathogenic bacteria transmitted through fluids or through the atmosphere are aerobic or facultatively anaerobic bacteria, which with a very few exceptions, contain the enzyme catalase. Similarly, catalase is present in most animal cells, as for example, in skin cells, erythrocytes, liver cells and kidney cells. Thus, urine and other body fluids may contain catalase, if cells, bacteria, or cell rupture products containing catalase are present. Thus, the presense of significant quantities of catalase would indicate that some unusual breakdown of catalase-containing cells is occurring or has occurred in the body, or that significant quantities or bacteria are present. It has been known that this enzyme is extremely specific in its ability to disproportionate hydrogen peroxide. The catalase content of bacteria, for example, is reported to be in the order of from 1 to 2 per cent of the total protein content thereof, which would be a quantity equivalent to about $10^3$–$10^4$ catalase molecules per organism.

It has been found that a polarographic membrane-type cell (an anode and a cathode in electrical circuit with each other through a suitable electrolyte, the cathode being adjacent to a thin outer wall of material permeable to oxygen) may be successfully employed to quantitatively detect an increase within a hydrogen peroxide solution of even less than $10^{14}$ molecules per $cm^3$ of oxygen, when this invention is employed. According to this invention the increase in oxygen partial pressure would result from the disproportionation of a hydrogen peroxide solution by admixture with a fluid containing catalase molecules therein. It has been determined that the accuracy of this measurement by the polarographic cell is not impaired by the presence of the hydrogen peroxide solution (or of a hydrogen peroxide-generating solution) in contact with a properly selected permeable membrane. Such a membrane should be impermeable to hydrogen peroxide, non-porous and have an $O_2$ permeability coefficient equal to or greater than $5 \times 10_{-11}$ gm/atmos-cm-sec.

The decomposition of hydrogen peroxide to oxygen and water in the presence of catalase as from bacteria or various animal cells is very rapid. The oxygen partial pressure of the peroxide solution itself rapidly increases at a rate proportional to the amount of catalase enzyme present and to the activity thereof. In the case of bacteria detection this increase in oxygen partial pressure is assumed to be proportional to the number of bacteria present in the hydrogen peroxide solution, when it is known that no other catalase source need be accounted for. Oxygen permeation through a permselective membrane in contact with a peroxide solution has been found to be linearly proportional to the solution partial pressure of oxygen in the peroxide solution itself. Oxygen gas entering through the oxygen-permeable membrane and contacting the cathode of the polarographic cell produces a cell current, which may be measured and recorded.

Determination of the oxygen generated by such a decomposition of hydrogen peroxide is accomplished by admitting the reactants (preselected volumes of sample fluid [reagent] and hydrogen peroxide [substrate]) into a reaction chamber and into contact with the exposed membrane of a polarographic cell. Oxygen liberation and detection enables a measure of the reaction velocity.

Ideally, when the reactants have been admitted, the volume of the reaction chamber will have been completely filled, closed and rendered non-expandable. Such an arrangement provides a large dynamic range of reaction velocity measurement. This follows from the fact that the liquid medium comprising reagent and substrate becomes increasingly supersaturated with oxygen as the reaction proceeds and, unless the system volume is unable to expand, oxygen gas bubble nucleation can occur at values of oxygen supersaturation as low as 0.3 atmospheres in excess of the oxygen pressure in the ambient atmosphere.

In less-than-ideal arrangement (as in the case of limitations in closure valves) the occurence of a very small area at the liquid-air interphase due to incomplete closure of the reaction chamber can be tolerated so long as the measurement of reaction velocity is accomplished before the oxygen supersaturation exceeds about 0.3 atmospheres above atmospheric.

This restriction on the time for measurement places a limitation in turn upon allowable mixing time and it is important to have as complete and as uniform a mixing of the reactants as possible to achieve a true reaction rate in the boundary layer over the cell membrane. Therefore, in a preferred embodiment of this invention initial mixing of the reagent and substrate is accomplished immediately prior to the introduction of these materials into the reaction chamber and this initial mixing is followed by further stirring within the reaction chamber.

BRIEF DESCRIPTION OF THE DRAWINGS

The exact nature of this invention as well as objects adn advantages thereof will be readily apparent from consideration of the following specification relating to the annexed drawing in which:

FIG. 1 is a schematic representation of an operative unit for catalase-detection in body fluids, e.g. urine for the detection and/or monitoring of pathological conditions;

FIGS. 2 and 3 set forth schematically other variations of the structure of FIG. 1;

FIG. 4 sets forth a schematic representation of a balanced double-cell bacteria detector with the electrical output of the two cells bucked against each other and the difference current being measured;

FIG. 5 schematically illustrates a balanced cell arrangement wherein separate reaction chambers are utilized with a double cell positively urged into sealing engagement with the base of the well structure;

FIGS. 6a, 6b and 6c are schematic representations of a sequence detection system for bacteria in the atmospheric ambient (including one means for establishing and locating a reproducible small volume of sample);

FIG. 7 shows a variation of the structure in FIG. 6c employing a second means for establishing and locating a reproducible small sample volume under testing conditions, and FIGS. 8a, 8b and 8c display several exemplary cathode configurations illustrating the requisite length to width ratio of the exposed cathode surface.

DESCRIPTION OF THE PREFERRED EMBODIMENT

Various embodiments of this invention are disclosed herein differing predominately in (a) how the sample is processed during testing for the presence of catalase, (b) how large a chamber is needed to test the sample and (c) what sensitivity of readout is desired. These factors in turn depend in large part upon the purpose for which the assessment of catalase activity is being made.

At present the prime application of this invention is for the detection and monitoring of pathological conditions of interest in medical practice (e.g. the testing of urine samples). A preferred embodiment for rapidly and effectively conducting such tests is shown in FIG. 1.

A pair of syringes 11, 12 providing preselected amounts of reagent (e.g. body fluid such as urine) from syringe 11 and substrate (hydrogen peroxide) from syringe 12 are adapted to be synchronously driven by common actuator 13 movable for a preselected distance in a straight line defined by the movement of guide rod 14 (attached thereto) through guide tube 16 in guide assembly 17. Guide assembly 17 also releasably supports syringes 11, 12. The different diameters of the barrels of syringes 11, 12 and the common stroke length for the piston of each syringe conveniently enable proportioning of the quantities of each liquid employed. A typical ratio is 10 parts of reagent to 1 part of hydrogen peroxide. The concentration of the hydrogen peroxide is selected so that upon dilution by mixing with the reactant the resulting solution will have a hydrogen peroxide concentration in the range of from 0.01 to 1 mole per liter for conduct of the reaction.

The catalase-$H_2O_2$ reaction is very specific, but a hydrogen peroxide solution, per se, need not be used. The hydrogen peroxide may be generated in situ by the addition of agents such as $NaBO_2 \cdot 3H_2O \cdot H_2O_2$, sodium perborate, to water or to the fluid sample.

Valve 18 is set so that reactant passes from syringe 11 via conduit 19 to conduit 20, when actuator 13 is depressed. At the same time substrate passes from syringe 12 via conduit 21 (valve 22 open). Conduits 20 and 21 empty into opposite ends of leg 23 of tee 24 where the reactant and substrate premix and pass through leg 25 into reaction chamber 26. The volume of solution admitted to reaction chamber 26 is such that with valve 27 closed and valve 28 open some of the solution spills over and out overflow tube 29.

The incoming solution is continuously mixed after it enters chamber 26 by agitator means 30, preferably a magnetic stirrer actuated by motor-driven magnet 31. The stirred solution should provide complete mixing in the boundary layer adjacent membrane 32 (e.g. polyethylene) of the membrane-type oxygen sensing polarographic cell 33. Cell 33 is an electrolytic device for use in chemical analyses and is of the general type described in U.S. Pat. No. 2,913,386—Clark, Jr., this patent being incorporated by reference. The anode 34 and cathode 36 of cell 33 are electrically connected through a "captive" electrolyte or an electrolyte-forming substance 37, which is protected from turbulence and is physically isolated and electrically insulated from the liquid sample to be analyzed by non-porous membrane 32 permeable to the oxygen, but not to hydrogen peroxide. Fill hole 33 is conveniently provided to enable changing of the electrolyte as desired. By way of illustration this hole is sealed with a ground glass stopper, however, other arrangements may be used. Membrane 32 extends over and is taut against the surface of platinum cathode 36 embedded in and supported by a plastic or glass rod, a specific cathode area being exposed at the distal end of the insulating electrode support rod in accordance with the improved construction of this invention.

The significant differences between the construction of the earlier polarographic cells (as typified by the device disclosed in U.S. Pat. No. 2,913,386) and the construction of the preferred cell for the practice of the instant invention are the configuration of the exposed portion of the cathode and the provisions made for securing a seal between the polarographic cell and the reaction cell construction. Both of these aspects are discussed in detail in description below.

If bacterial catalase is present in the sample, a very rapid decomposition (to oxygen and water) of the hydrogen peroxide occurs and the partial pressure of oxygen in the peroxide solution increases rapidly (in about ¼–5 minutes) at a rate proportional to the amount of catalase enzyme present and to its activity. The extent of diffusion of this oxygen through the membrane 32 into cell 33 is linearly proportional to the oxygen partial pressure in the adjacent hydrogen peroxide solution and the entering oxygen upon reaching the cathode produces a cell current that is measured and then amplified by ammeter amplifier 39 for direct readout of the catalase activity and/or final recording of a graphic representation of oxygen partial pressure as a function of time on potentiometer-recorder 41. The catalase activity is expressed in catalase activity units, such a unit being defined as that amount of catalase activity, which will decompose 1 micromole of hydrogen peroxide per minute at some specified temperature and hydrogen peroxide concentration. The aforementioned conditions may, for example, be 37° C and 0.1 moles per liter of hydrogen peroxide concentration.

A platinum electrode (0.02 inch diameter wire embedded in plastic) is bent at its upper end being extended substantially parallel to membrane 32. The plastic and part of the metal is ground away to expose a flat, long, thin cathode area (about 0.002 × 0.0625 inch). This cathode 36 is tightly covered with 0.001 inch thick polyethylene membrane (membrane 32) which retains the potassium chloride electrolyte (0.3-3M) in the cell 33. Both the cathode 36 and the silver-silver chloride anode 34 are electrically connected to ammeter-amplifier 39 and have a predetermined electrical potential applied thereacross from a power source such as battery 42. The simplified overall reaction is:

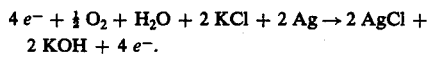

A relatively large volume of electrolyte is provided in cell 33 to minimize the effect of electrolyte change and such cells will perform in a stable manner for as long as one year. The inherent sensitivity of the detecting device is at least $2.71 \times 10^{-7}$ amps/atmosphere of oxygen partial pressure.

Spontaneous hydrogen peroxide decomposition may be avoided by using a sufficiently clean system. However, if desired a buffered stabilizer may be added to the solution, e.g. acetanilide buffered slightly acidic (pH 6.8) with 0.1M phosphate buffer.

The sensitivity of cell 33 in determining the solution oxygen content in the hydrogen peroxide solution is determined principally by both the permeability characteristics of membrane 32 relative to oxygen and by the dimensions of the surface of cathode 36 exposed to the oxygen passing through the membrane 32. Looking down at the upper end of the cathode structure, the electrode appears as a substantially long thin straight or curved area having a length to width ratio of at least 25:1 and preferably 100:1 with the width thereof being less than about 0.005 inch and preferably less than 0.002 inch. Although the membrane 32 preferably employed is polyethylene, any membrane material that can be produced as a sound (non-porous) very thin membrane, is impermeable to $H_2O_2$ and has an $O_2$ permeability coefficient equal to or greater than $5 \times 10^{-11}$ gm/atmos-cm-sec may be used.

The pre-mixing device (e.g. tee 24) through which the reactants pass and mix prior to entering the reaction chamber 26 should be placed as close as feasible to the reaction chamber so that the rapidly ensuing reaction does not proceed too far before measurements can be made. These measurements must, of course, be made when the solution is actually in reaction chamber 26 with continued mixing by agitator 30.

Manifestly for even greater accuracy in measurement of the reaction rate pre-mixing devices may be used that more completely subdivide the substrate and fluid sample flows immediately prior to their mixing contact.

Although it is preferred that all of valves 18, 22, 27 and 28 be closed as soon as reaction chamber 26 has been filled in order to provide a completely filled, closed, non-expandable reaction volume, limitations in valve construction and operation may require that the last valve to have been closed (valve 28) be left open. All of conduits 20, 21, 29 and drain line 43, are normally very small diameter tubes (long length relative to diameter). Therefore, leaving the overflow valve 28 open to the atmosphere (all other lines closed) introduces but a very small liquid-air interphase (e.g. less than 0.1 inch in diameter). This magnitude of liquid-air interphase only becomes of concern, because of loss of dynamic range of measurement, when samples of such high catalase activity are encountered that the oxygen partial pressure exceeds the nucleation level before the measurement can be taken. The level of concern lies at about 3 catalase activity units at present.

Assembly and disassembly of the device is facilitated by couplings 44 and 46. Coupling 46 urges the membrane-covered end of cell 33 into sealing engagement with recess 47 of housing 48 via annular seal 49.

Other arrangements of reaction chamber structures in combination with oxygen-detection cells are shown in FIGS. 2 and 3. In the structure shown in FIG. 2 housing 51 is removably affixed to base 52 by fastening means such as screws 53 to define reaction volume 54 in communication with oxygen cell 56 via membrane 57 forming part of the wall area defining volume 54. Valved connections (58, 59, 61) are shown communicating with the interior of volume 54. These respective connections are used to provide for (a) the introduction of $H_2O_2$ solution (both for the catalase-$H_2O_2$ reaction and for flushing out volume 54 between tests) from $H_2O_2$ solution source 62, (b) the introduction of sample fluid (e.g. urine, synovial fluid, etc.) from sample source 63 and (c) air elimination (to preclude liquid-air interphase), and (d) reaction product flush-out from overflow tube 64. Hypodermic syringes are shown as convenient means for the introduction of sample fluid and $H_2O_2$ solution on demand. The sealing off of volume 54 is insured by deformable annular seal 66 and drainage of the reaction volume is facilitated by drain line 67 and valve 68.

In the structure shown in FIG. 3 the reaction sample volume 71 is defined by housing 72 through the walls of which extend valve connections 73, 74, 76 and 77 and small stirrer shaft 78. Although for convenience the agitator means has been shown as a shaft-propeller combination, it is preferred to use a stirrer of the magnetic type as shown in FIG. 1, which does not require penetration of the wall of housing 72. Deformable seal material 79 is disposed between housing 72 and base 81 releasably fastened together as, for example, by screws 82. $H_2O_2$ solution is introduced on demand into volume 71 from source 83 and sample fluid to be tested for catalase activity is introduced when required into volume 71 from source 84. As in the case of the device shown in FIG. 1 the volumes of the source of sample and substrate are proportioned so that the volume of substrate preferably is less than about 10% by volume of the sample although this is not a positive requirement. Wash fluid is forcibly introduced into housing 72, when required from source 86, all of sources 83, 84 and 86 conveniently being indicated as hypodermic syringes. The fluids admitted to reaction-sample volume 71 are agitated by stirrer 87 on demand to minimize or eliminate concentration gradient in the fluid and overflow 74 is used to eliminate air (and thereby eliminate liquid-air interphase). Drain 88 is provided for removing the contents of volume 71 during flush-out. Membrane-covered $O_2$ detection cell 89 is disposed in cooperation with the reaction-sample volume 71 in the same manner as cell 56 relative to volume 51 (FIG. 2).

Arrangements for increasing system discrimination are schematically shown in FIGS. 4 and 5. In the device of FIG. 4, two membrane-type oxygen cells 91, 92 are employed. The electrical outputs of cells 91 and 92 are bucked against (in series opposition with) each other in the electrical arrangement shown and the difference current is measured. By adjusting potentiometer 93 and variable resistor 94 so that the reading on the recorder 96 is zero prior to the conduct of catalase activity determinations, the effects of all parameters similarly affecting cells 91 and 92 will be nullified. Thereafter, the current outputs from cells 91 and 92 during simultaneous determinations of oxygen gas generation will reflect the difference in the current outputs from these two cells. Although cells 91, 92 are shown in communication with the same chamber, separate chambers (one for each $O_2$ detection cell as shown in FIG. 5) can be employed so long as there is good thermal contact between the cells to preserve identical temperature conditions.

In this manner those variables (temperature and absolute level of $pO_2$ in the fluid) that affect both cells in the same manner are cancelled out. Further, this arrangement permits the conduct of differential testing wherein two identically collected samples of bacteria having the same background contamination may be differently treated. Thus, for example, a sample isolated on filter disc 97 as described hereinbelow in connection with FIGS. 6 and 7 may be treated to inactivate the catalase content thereof by heating or by the addition of chemicals which specifically inhibit catalase, while the sample similarly isolated on filter disc 98 may remain untreated. Assuming that the inactivating agent does not inactivate other catalytic agents for $H_2O_2$ decomposition (e.g. iron oxides) as may be present, these catalytic agents decompose an equal amount of $H_2O_2$ in both filter discs (97 and 98). These outputs balance out while the inactivated catalase does not produce any $H_2O_2$ decomposition to balance the $H_2O_2$ decomposition of the unaltered catalase thereby a differential output results, which is measurable by microvoltmeter 99 and recordable by recorder 96.

Filter discs 97 and 98 are positively urged against membranes 101 and 102 of oxygen cells 91 and 92, respectively, by the spring loading of filter holders 103, 104. The spring-loaded filter holders 103 and 104 are mounted in positioning plate 106 covering chamber 107 in well unit 108. The walls of well unit 108 may be made of glass or plastic, but is preferably made of transparent material, as for example plexiglass. Hydrogen peroxide solution is introduced into chamber 107 either prior to filter insertion or through passage 109 from a hydrogen peroxide reservoir (not shown).

The oxygen detection cells of this invention are formed with the upper portion thereof contoured to facilitate sealing between the oxygen cell and the well unit. In each of the embodiments shown the upper membrane-covered portion of the oxygen-detection cell is made in the shape of a truncated cone and because of the disposition of the membrane is in sealing engagement with matching countersunk recess extending through the bottom of the structure forming the reaction chamber.

Improved detectability of oxygen partial pressure results from this use of balanced oxygen cells, because it becomes possible with this arrangement to measure the current output with higher sensitivity.

Thus, for example, at atmospheric oxygen partial pressure (0.21 atmosphere) a single oxygen cell of the type described herein provides a current output of approximately $5.7 \times 10^{-8}$ amperes. When using a single cell, the sensitivity available for current measurement is necessarily limited to this order of magnitude. By bucking two cells together, the useable sensitivity is limited only by the amount of system random noise. In place of the second cell of FIG. 4 a constant bucking voltage output source could be employed, but this arrangement would offer the opportunity to only partially compensate for temperature and absolute level of oxygen partial pressure and does not provide opportunity for differential or comparative testing.

A double oxygen detection cell 121 in a single envelop 122 for electrical connection in series opposition is shown in FIG. 5. A pair of adjacent reaction chambers 123, 124 are provided, each in oxygen detection communication with one of cathodes 126, 127 as shown. Cathodes 126, 127 are electrically connected to common anode 128 (connected to the positive terminal of battery 129) through a common reservoir 130 of electrolyte. Collar 131 threadably engagable with base 132 positively urges cell 121 into sealing engagement with base 132 in recesses 133, 134. Base 132 is preferably made of a material which is a good thermal conductor in order to aid in maintaining the cathode legs of cell 121 at the same temperature. Walls 136 and top 137 are preferably of a transparent non-metallic material inert to oxidation.

Reservoir 138 receives the fluid test sample, which may be simultaneously pumped by pump 139 into both reaction chambers 123, 124 via the valved conduits shown. Reservoir 141 contains $H_2O_2$ solution, which may be simultaneously pumped by pump 142 into both reaction chambers 123, 124 via the valved conduits shown. Reaction chambers 123, 124 are vented by valved conduits 143, 144 respectively and reservoir 146 may contain a catalase inhibitor, as for example 2% $H_2SO_4$, which can be introduced on demand into chamber 123 by the pump 147.

In operation, identical portions of a urine sample are admitted to reaction chambers 123, 124 filling most of the volume thereof. A small amount of inhibitor is introduced to suppress the catalase activity in reaction chamber 123 and potentiometer 148 is set to provide a zero reading on recorder 149, the electrical outputs of cathodes 126, 127 being in series opposition. Thereafter, when $H_2O_2$ solution is simultaneously introduced to reaction chambers 123, 124, the measured increase in oxygen partial pressure will accurately reflect the catalase activity properly compensated for temperature and quiescent oxygen content.

An atmospheric bacteria detection arrangement is shown in FIGS. 6a, b and c in which bacteria from the ambient are impacted on filter disc 161 attached to filter holder 162 by drawing in air from the atmosphere through a high volume impaction orifice 163 with pump 164. After a given period of operation, filter holder 162 is removed from housing 166, a catalase-free liquid, as for example sterile water, is added to filter disc 161 and the wet filter disc is then subjected to ultrasonic energy by placing it in contact with ultrasonic transducer 167 to rupture the bacteria cell walls, transducer 67 receiving power from ultrasonic generator 168. Other means may be employed for rupturing the cells and releasing the soluble components therefrom, for example, detergents or lysing enzymes may be employed. By this lysing action the intracellular catalase enzyme is effectively exposed. With most types of bacteria penetration of the unlyzed bacterial cell by $H_2O_2$ readily occurs and this lysing step may be omitted.

Filter holder 162 with processed filter disc 161 held thereby is then inserted into chamber 169 of housing 170 with the filter disc 161 being disposed in intimate contact with polyethylene membrane 171 of the membrane-type oxygen detection polarographic cell 172.

If desired, instead of impacting the bacteria directly on filter disc 161, the impaction may be conducted in a liquid and then the bacteria may be transferred to a filter disc by filtering the liquid therethrough.

When it is desired to detect very small numbers (e.g. about 100 or fewer) of bacteria or other cells with measurable partial pressure increase it is critical that the volume of hydrogen peroxide solution in actual contact with the reactant be kept very small, preferably less than 0.1 cc. One very effective means for establishing such a reproducible small reaction volume, which can be effectively located adjacent the oxygen electrode 173 is by the use of a small body of cellulose acetate-or cellulose nitrate-type filter material or similar groups material for the disc 161. In the apparatus of FIG. 6c filter disc 161 is sandwiched between membrane 171 covering electrode 173 (cathode) and the oxygen-impermeable supporting structure 174 disposed directly behind filter disc 161 and holding it in the proper position in chamber 169.

The hydrogen peroxide solution is injected into chamber 169 carefully through small opening 175 so that organisms, which may be present on and in filter disc 161, are not dislodged. Similar results can be effected by having the hydrogen peroxide solution covering the bottom of chamber 169 before insertion of the filter holder 162 and disc 161 into chamber 169 in which case the filter disc 161 becomes wet during fairly rapid immersion.

Once filter disc 161 is wet, convective mixing between the volume defined by disc 161 and the surrounding hydrogen peroxide solution is effectively limited, but molecular diffusion into the filter disc 161 from the surrounding peroxide solution remains about the same as in the case of a free liquid. Consequently, the lateral diffusion path for evolved $O_2$ gas to escape from the volume of filter disc 161 is comparatively long while the diffusion path to the oxygen electrode 173 is comparatively short. Thus, the oxygen partial pressure generated by the presence of bacteria (or other catalase source) with resultant hydrogen peroxide decomposition is effectively trapped adjacent the oxygen sensitive electrode 173 within the filter disc volume and can build up to relatively high values. Also, this high oxygen supersaturation ranging from about 0.01 to at least 1 atmosphere depending on the amount of catalase present can be maintained for long periods of time. Any cell current generated is measured directly by ammeter 176, this measured current being amplified by amplifier 177 may, if desired, be recorded on potentiometer recorder 178.

A different arrangement for the reproducible small sample volume is shown in FIG. 7. A filter disc 181 is set in a recess in the removable supporting structure 182 shown in place in chamber 183 in well housing 186. This arrangement provides greater isolation for the volume of sample being processed. The structure of $O_2$ membrane cell 187 is substantially the same as that of the other polarographic cells except for the provision of different means for adding electrolyte (access tube 188). Hydrogen peroxide solution is carefully introduced into chamber 183 via channel 189 extending through filter holder 190. Although provision therefor is not shown hydrogen peroxide may instead be introduced into chamber 183 prior to the introduction of the filter disc 181 and structure 182. Oxygen gas generated in the reaction volume of filter disc 181 permeates membrane 191 and, after it has entered cell 187, has moved to cathode 192 and picked up electrons, a current is generated, which is sensed by the low impedance input micro-microammeter amplifier 193 and recorded by potentiometer recorder 194.

To illustrate the detection sensitivity that can be achieved with the small reproducible sample volume of this invention (whether defined by a quantity of porous material or by positive isolation of the catalase-$H_2O_2$ reaction) consider a practical filter disc 150 microns thick having a diameter of 0.5 cm (or 0.196 $cm^2$ in area) having approximately 80 percent voids. This will provide a sample volume, or solution volume, of $2.38 \times 10^{-3} cm^3$ in the filter disc. Using the following relationship:

$$N = 2.68 \times 10^{19} v V(pO_2) \qquad (1)$$

wherein
  $N = $ the number of oxygen molecules in a given volume ($V$ in $cm^3$) of aqueous solvent;
  $pO_2 = $ the oxygen partial pressure in atmospheres produced by these N molecules; and
  $v = $ the absorption coefficient, for oxygen. This would be the volume of oxygen (when reduced to 0° C and 760 mm of mercury) absorbed by one cc. of test solution when the pressure of the oxygen without the aqueous tension, amounts to 760 mm of mercury.

If the absorption coefficient ($v$) for oxygen in dilute hydrogen peroxide solution is taken to be 0.028 at 20°C then —

$$N = 7.5 \times 10^{17} V(pO_2) \qquad (2)$$

Assuming that a total of N molecules of oxygen are produced by a given number ($n$) of bacteria, each of which produces substantially the same number ($\alpha$) of molecules of oxygen during the catalase-peroxide reaction in the cell, the above relation becomes $$n\alpha = 7.5 \times 10^{17} V(pO_2) \qquad (3)$$

As reported in the article "Crystalline Bacterial Catalase" by D. Herbert and J. Pinsent, (Biochem. J. 43, 1948) $1.9 \times 10^7$ molecules of $H_2O_2$ is decomposed per catalase molecule per second with $10^3$–$10^4$ catalase molecules being made available by each aerobic bacterium. By allowing the reaction to proceed for 100 seconds, the oxygen production per bacterium would be greater than $10^{12}$ molecules of oxygen. Employing this value ($10^{12}$) for $\alpha$ and with $2.38 \times 10^{-3} cm^3$ as the hydrogen peroxide solution volume in the above equation (3) yields a value of $5.6 \times 10^{-4}$ atmosphere of oxygen liberated per bacterium. This significantly large oxygen partial pressure for a single bacterium enables the quantitative determination of the presence in a fluid of fewer than 100 bacteria utilizing the improved cell construction disclosed herein.

Experiments with unlysed aerobically-grown $E.$ $coli$ have provide $\alpha$ values ranging from $5 \times 10^{10}$ to $2 \times 10^{12}$ molecules oxygen produced in 2 minutes per bacterium using 0.1 molar $H_2O_2$ solution. Other bacteria may be similarly evaluated and undoubtedly there will be variations between different bacteria. For example, $E.$ $coli$ are considered to have a relatively low catalase content. A value of a greater than $10^{11}$ molecules of oxygen per unlysed bacterium would make the use of lysing enzymes or ultrasonic energy unnecessary except when it becomes necessary to detect very small numbers (less than 100) bacteria. However, for values of $\alpha$ of less than $10^{11}$ molecules of oxygen per bacterium lysing is preferred, in which case the filter disc method of collection and presentation makes the application of ultrasonics energy (as described in connection with FIG. 6) to the bacteria particularly convenient. The moistened filter disc need only be monomentarily brought into contact with an ultrasonic energy source to provide excellent energy coupling to the bacteria. A very short exposure time is all that is required for effective lysing action by this procedure.

It is also proposed that this invention can be applied to automatic quantitative determination of catalase content, as for example, by the use of a moving web or tape (or, if desired, a continuous tape) to pass in sequence through the steps of sampling, lysing, reaction development and measurement at subsequent stations. The tape could comprise a layer of a thin porous medium, as for example cellulose acetate or agar, supported on a base of low oxygen permeability as, for example, a relatively thick (e.g. greater than 20 mils) plastic material. Although continuous motion of the tape is possible, incremental motion thereof is more practical. For example, in the detection of bacteria content in the atmosphere in a 5 minute cycle a discrete portion of the porous media would first be subjected to impact sampling over a period of about 2 minutes at a first station; this discrete portion of the tape would then be advanced in order to subject the sample to ½ minute of lysing by means of ultrasonic energy at a second station and finally the tape would be moved to a third station, where the initiation of, measurement and recording and/or transmission of the results of the reaction according to this invention would occur.

The inherent sensitivity of the catalase-hydrogen peroxide reaction as employed in this invention may be improved even further as, for example, by employing a small thin disc of agar, or similar material which can be selectively rendered fluid, as the initial sampling medium. Sampling is initially accomplished on a given disc of agar. This first disc of agar is then heated to the fluid state and the resultant fluid is filtered through a fibrous filter idsc of smaller cross-sectional area than the agar disc thereby providing further concentration of the collected bacteria. For example, an initial 25 millimeter diameter disc of agar used to collect an initial sampling of bacteria would provide a concentration of 25 to 1 by subsequently heating the agar and filtering the resultant liquid through a 5-millimeter diameter fibrous filter disc.

As has been stated hereinabove an aspect of this invention of considerable importance is the increased sensitivity offered by the use of an exposed long, thin cathode area, that is, an area having a length to width ratio of at least 25:1. Examples of various useful configurations have been shown in FIGS. 8a, 8b and 8c. These are views of the surface of a glass-enclosed cathode 201 as "seen" by the oxygen-permeable membrane. One manner in which such cathode areas may be prepared is to bend and end tab 202 of the upwardly extending cathode wire (e.g. platinum, gold) at right angles and, for the configurations shown in FIGS. 8b, 8c, to bend these tabs in an arc, zig-zag or other form and then encase the entire wire in an electrically non-conducting support, e.g. glass or plastic. Thereafter, by grinding away the support and part of the metal, a metallic area of long, narrow configuration (203, 204, 206) is exposed.

In those situations in which a time lapse between sampling and measurement can be tolerated nutrients may be impregnated into a bacteria sample collected on a filter disc, for example, to promote the growth of any bacteria present therein or growth inhibitor may be added for the opposite effect. As a use for this capability, one of two simultaneously collected samples (or of two portions of the same sample) may be treated so as to inhibit bacterial growth thereof as, for example, by the use of antibiotics. The growth of the untreated sample will increase the catalase activity thereof and a comparison between the catalase activity of the two samples thereafter will provide a rapid indication of the effectiveness with which the antibiotic will attack the bacteria. A high reading of differential current output will indicate high sensitivity of the bacteria to that antibotic. Inhibitors and media that selectively retard or promote a given species of bacteria also may be used for bacteria identification. Long term (at least 24 hours) organism growth as is required for colony development in conventional microbiological culturing is not required for these sensitivity or indentifying tests, because with the high system sensitivity available with the oxygen membrane cell of this invention, a single bacteria growth doubling time (20–60 min.) should be easily detectable and sufficient to observe the effect of the retardation or inhibition.

In summary, catalase-activity detection apparatus and methods have been demonstrated, which quantitatively and rapidly measure the incremental generation of oxygen partial pressure directly in a $H_2O_2$ solution, where the inherent catalase content of various animal cells causes the rapid decomposition of $H_2O_2$ to oxygen and water. The apparatus disclosed affords the opportunity for dynamic and continuous observation of the catalase-$H_2O_2$ reaction by providing for the quantitative measurement of catalase activity.

Means have been developed and disclosed for limiting, if desired, the effective hydrogen peroxide solution-sample volume (less than about 0.1 cc) involved in the detection sequence. The simplicity of the instrumentation disclosed herein and the rapidity with which quantitative catalase activity can be measured and recorded make this invention very useful as a clinical tool. For example, it is highly desirable to have the capability for inexpensive, rapid mass screening to diagnose urinary infections before they become symptomatic. When a test of a patient's urine by the method of and with a device constructed according to this invention indicated significant catalase activity, it is then necessary only to make more definite tests to determine whether the large catalase activity is due to the presence of bacteria or whether unusual breakdown of catalase-containing cells is occurring or has occurred within the patient's body.

When a urinary infection has already been diagnosed, bacteria and other cells present in the urine are first filtered out. Next, a test is run to determine catalase activity of the filtered urine. If the test is positive, this is evidence that a breakdown of catalase-containing cells (inflammation, for example) is occurring in the body.

Also, a balanced double cell arrangement has been devised that provides a more sensitive measurement of the change in oxygen partial pressure in a hydrogen peroxide solution by cancelling out any variation due to spontaneous hydrogen peroxide decomposition and temperature effects. This is particularly important because of the temperature sensitivity (about 5%/°C) for $O_2$-detecting cells of the type disclosed.

Also, te use of a pair of $O_2$-membrane cells connected in series opposition and sensing $O_2$ permeating from different fluids one of which is a reference fluid free of catalase activity, such as water for example, is proposed. By subjecting both the cells and fluid content to the same temperature conditions and then adjusting the potentiometer recorder to zero before adding $H_2O_2$ solution to both the sample fluid, and the reference fluid, both temperature and quiescent oxygen content are eliminated as variables.

Further, the balanced cell arrangement permits the measurement of catalase activity in the presence of other possible hydrogen peroxide decomposing agents, which may have been collected in the sampling process by conducting the measurement on two simultaneously collected samples, one of which is selectively treated to inactivate the catalase, without altering the activity of other $H_2O_2$ catalyst in that same sample.

An impaction method for separating bacteria from the atmosphere by depositing them directly onto a small filter is described by which a sufficient number of bacteria can readily be collected in a short period of time to provide a detectable response in the hydrogen peroxide system of this invention. By the use of a small filter disc a sampling can be conveniently secured from fluids containing bacteria enabling an added capability for concentrating bacteria for insertion into a small reaction volume.

What I claim as new and desire to secure by Letters Patent of the United States is:

1. A process for the clinical detection of the catalase activity in catalasa-containing cells in body fluid by dynamic monitoring of oxygen gas produced by the catalase-peroxide reaction comprising the steps of:
   a. secruing a quantity of body fluid of unknown catalase content,
   b. intorducing a predetermined volume of said body fluid into a non-expandable reaction volume separated by an oxygen permeable membrane from electrochemical measuring means, said electrochemical measuring means being in association with said oxygen permeable membrane said means being totally outside said closed reaction volume, said membrane being impermeable to hydrogen peroxide and having an oxygen permeability coefficient of at least about $5 \times 10^{-11}$ gms./atmos.-cm.-sec.,
   c. introducing a predetermined quantity of hydrogen peroxide solution into said reaction volume such that the volumes of said body fluid and hydrogen peroxide solution completely fill said reaction volume and such that the resulting solution has a hydrogen peroxide concentration in the range of from 0.01 to 1 mole per liter of said resulting solution, closing said reaction volume and
   d. electrochemically measuring the increase of partial pressure of oxygen in said reaction volume by measuring the extent of diffusion of oxygen through said membrane, said extent of diffusion of oxygen through said membrane being linearly proportional to said partial pressure of oxygen in said reaction volume.

2. The process for the clinical detection of the presence of catalase-containing cells in said body fluid as recited in claim 1 wherein the volume of hydrogen peroxide solution introduced does not exceed about 10% of the volume of said body fluid.

3. The process for performing rapid, quantitative determination of catalase content by dynamic monitoring of the oxygen gas produced by the catalase-peroxide reaction comprising the steps of:
   a. isolating two substantially identical separate portions of material of unknown catalase content in solution to be tested for catalase activity,
   b. introducing a predetermined volume of each of said portions of said material into first and second reaction volumes, each of said reaction volumes being non-expandable and each being separated by an oxygen permeable membrane from a polarographic cell connected in series opposition, each said membrane being adjacent to the cathode of said cell and being impermeable to hydrogen peroxide and having an oxygen permeability coefficient of at least about $5 \times 10^{-11}$ gms./atmos.-cm.-sec.,
   c. inactivating the catalase content of one of said portions of said material without affecting the activity of other catalytic agents for hydrogen peroxide decomposition,
   d. introducing a predetermined volume of identical hydrogen peroxide solution into both said reaction volumes such that the volumes of said material and hydrogen peroxide completely fill each of said reaction volumes and such that the resulting solution in each said reaction volume has a hydrogen peroxide concentration in the range of from 0.01 to 1 mole per liter of said resulting solution, closing said reaction volumes, said polarographic cell being totally outside said closed reaction volumes, and
   e. measuring the difference between the increase of partial pressure of oxygen in said reaction volumes by means of said polarographic cell by measuring the extent of diffusion of oxygen through each said membrane, said extent of diffusion of oxygen through each said membrane being linearly proportional to the corresponding said partial pressure of oxygen in said reaction volumes.

4. The process for performing rapid, quantitative determinations of catalase activity as recited in claim 3 wherein the volume of hydrogen peroxide solution added does not exceed about 10% of the volume used of each of said portions of material.

* * * * *